United States Patent [19]

Owen et al.

[11] Patent Number: 4,633,027
[45] Date of Patent: Dec. 30, 1986

[54] PROCESS FOR CONVERTING OLEFINS TO GASOLINE, DISTILLATE AND ALKYLATE LIQUID HYDROCARBONS

[75] Inventors: Hartley Owen, Belle Mead; Samuel A. Tabak, Wenonah; Bernard S. Wright, East Windsor, all of N.J.

[73] Assignee: Mobil Oil Corporation, New York, N.Y.

[21] Appl. No.: 779,373

[22] Filed: Sep. 23, 1985

[51] Int. Cl.$^4$ ................................................ C07C 2/00
[52] U.S. Cl. .................................... 585/314; 585/331; 585/332; 585/415; 585/533; 585/709; 585/733; 585/723
[58] Field of Search ............... 585/314, 331, 332, 709, 585/733, 415, 533, 723

[56] References Cited

U.S. PATENT DOCUMENTS

| | | | |
|---|---|---|---|
| 3,969,426 | 7/1976 | Owen et al. ........................ | 585/640 |
| 3,972,958 | 8/1976 | Garwood et al. .................. | 585/469 |
| 4,048,250 | 9/1977 | Garwood et al. .................. | 585/469 |
| 4,150,062 | 4/1979 | Garwood et al. .................. | 585/415 |
| 4,211,885 | 7/1980 | Banks ................................... | 585/415 |
| 4,262,155 | 4/1981 | Hutson, Jr. ......................... | 585/331 |
| 4,423,274 | 12/1983 | Daviduk et al. .................. | 585/640 |
| 4,450,311 | 5/1984 | Wright et al. ..................... | 585/413 |
| 4,482,772 | 11/1984 | Tabak ................................. | 585/254 |
| 4,497,968 | 2/1985 | Wright et al. ..................... | 585/304 |
| 4,506,106 | 3/1985 | Hsia et al. .......................... | 585/312 |
| 4,543,435 | 9/1985 | Gould et al. ...................... | 585/330 |
| 4,547,602 | 10/1985 | Tabak ................................. | 585/314 |

Primary Examiner—Asok Pal
Attorney, Agent, or Firm—A. J. McKillop; M. G. Gilman; L. G. Wise

[57] ABSTRACT

A continuous process for upgrading $C_3$–$C_4$ hydrocarbon feed containing olefins to produce heavier liquid hydrocarbons comprising converting a major portion of $C_3$–$C_4$ olefins in an oligomerization zone by contacting a shape selective medium pore zeolite catalyst at elevated temperature and pressure to make distillate and olefinic gasoline; fractionating the oligomerization stage effluent to provide distillate and gasoline product and a $C_3$–$C_4$ intermediate stream containing isobutane and unconverted propene and butylene; and combining the $C_3$–$C_4$ intermediate stream with a portion of $C_3$–$C_4$ feed and further converting the combined streams in an alkylation zone to make heavier paraffinic hydrocarbons.

The olefin feed may be produced by catalytically converting methanol or similar oxygenated hydrocarbons in a known process.

4 Claims, 3 Drawing Figures

PROCESS FOR CONVERTING OLEFINS TO GASOLINE, DISTILLATE AND ALKYLATE LIQUID HYDROCARBONS

BACKGROUND OF THE INVENTION

This invention relates to an integrated system for converting oxygenates, such as methanol or dimethyl ether (DME), to liquid hydrocarbons. In particular it provides a continuous process for producing hydrocarbon fuel products or the like by converting the oxygenate feedstock catalytically to an intermediate lower olefinic stream, oligomerizing olefins and alkylating isobutane or other isoparaffins with olefins to produce light distillate and/or gasoline products.

In order to provide an adequate supply of liquid hydrocarbons for use as synfuels or chemical feedstocks, various processes have been developed for converting coal and natural gas to gasoline and distillate. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for making diesel fuel by a multi-stage technique.

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of new industrial processes.

The medium pore ZSM-5 type catalysts are useful for converting methanol and other lower aliphatic alcohols or corresponding ethers to lower olefins and also for oligomerizing olefins. Particular interest has been directed to a catalytic process for converting low cost methanol to valuable hydrocarbons rich in ethene and $C_3+$ alkenes. Various processes are described in U.S. Pats. Nos. 3,894,107 (Butter et al), 3,928,483 (Chang et al), 4,025,571 (Lago), 4,423,274 (Daviduk et al), 4,433,189 (Young), and 4,543,435 (Gould and Tabak), incorporated herein by reference. It is generally known that the MTO process can be optimized to produce a major fraction of $C_2$–$C_5$ olefins. Prior process proposals have included a separation section to recover ethene and other gases from byproduct water and $C_5+$ hydrocarbon liquids.

SUMMARY OF THE INVENTION

It has been discovered that methanol, DME or the like may be converted to liquid fuels, particularly gasoline, aliphatic distillate and alkylate, in a multi-stage continuous process, with integration between the major process units providing an alkylate product stream from $C_3$–$C_4$ aliphatics produced by primary stage zeolite catalysis. The initial stage MTO process hydrocarbon effluent stream, after byproduct water separation and fractionation can be partially fed to an oligomerization stage and an alkylation stage for conversion to heavier hydrocarbons. Ethene may be recovered by interstage separation and recycled and coreacted with methanol/DME or other oxygenates in the presence of ZSM-5 type catalysts.

In a preferred embodiment, the invention provides improved processes and apparatus for an integrated continuous technique for converting lower olefins (e.g., $C_2$–$C_5$) to liquid alkylate hydrocarbons comprising methods and means for prefractionating the olefinic feedstock to obtain a gaseous stream rich in ethylene and an olefinic stream containing $C_3+$ olefin;

contacting a major portion of the $C_3+$ stream from the prefractionating step with shape selective medium pore zeolite oligomerization catalyst in a distillate mode catalytic reactor zone at elevated temperature and pressure to provide a heavier hydrocarbon effluent stream comprising distillate, gasoline and lighter hydrocarbons;

fractionating the effluent stream to recover distillate, gasoline and $C_3$–$C_4$ hydrocarbon stream containing isobutane;

further reacting isobutane from the $C_3$–$C_4$ hydrocarbon stream with a second portion of $C_3+$ olefin from the prefractionating step in an alkylation reactor zone in the presence of acid alkylation catalyst to produce $C_7+$ alkylate.

Other objects and features of the invention will be seen in the following description and drawings.

THE DRAWINGS

DESCRIPTION OF PREFERRED EMBODIMENTS

Figure 1:
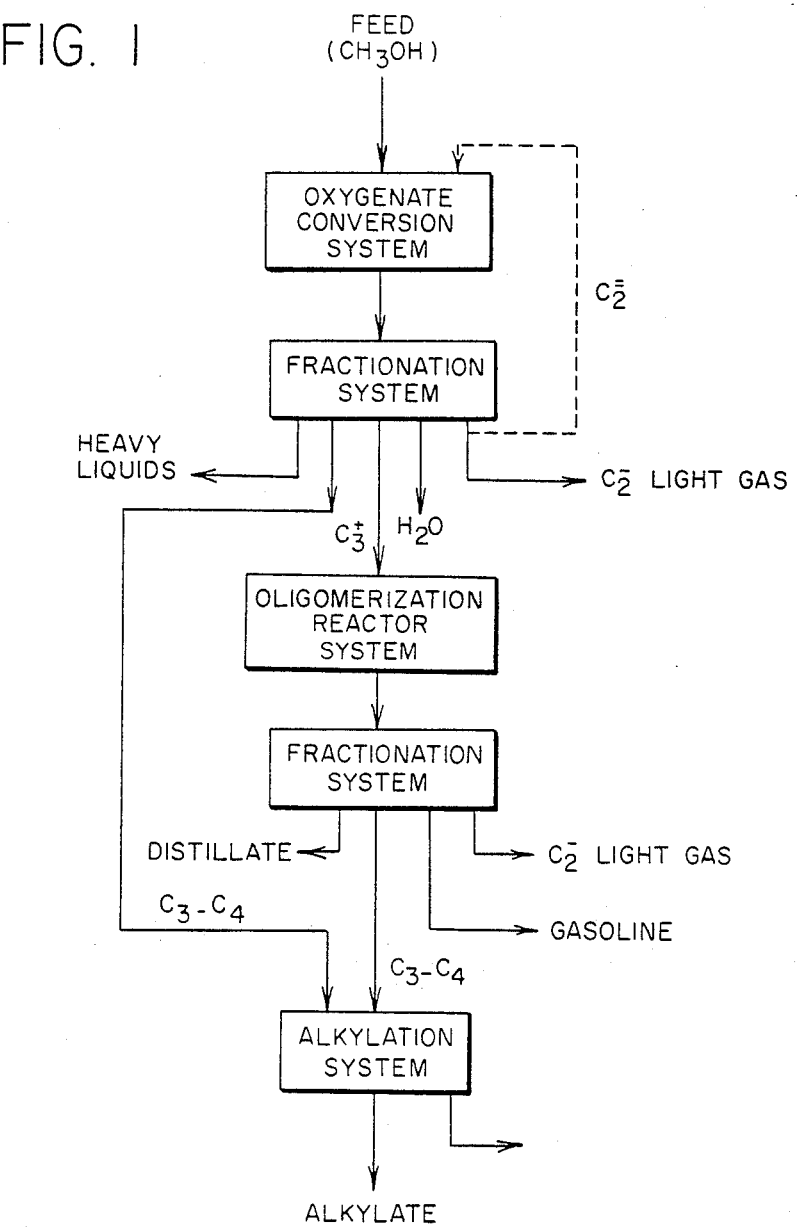
FIG. 1 is a process flow sheet showing the major unit operations and process streams.

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($CH_3OH + CH_3OCH_3 + H_2O$) is produced by partial dehydration. This reaction takes place in either conversion of methanol to lower olefins (MTO) or methanol to gasoline (MTG).

The zeolite catalysts preferred for use herein include the crystalline aluminosilicate zeolites having a silica to alumina ratio of at least 12, a constraint index of about 1 to 12 and acid cracking activity (alpha) of about 1–200. Lower acid zeolites (alpha = 1–50) are preferred for the MTO conversion and higher activity (alpha = 50–200) is preferred for oligomerization. Representative of the ZSM-5 type zeolites are ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for oxygenate conversion is HZSM-5 zeolite with alumina binder. These medium pore shape selective catalysts are sometimes known as porotectosilicates or "pentasil" catalysts.

Other catalysts and processes suitable for converting methanol/DME to lower olefins are disclosed in U.S. Pat. No. 4,393,265 (Bonifaz), U.S. Pat. No. 4,387,263 (Vogt et al.), and European Patent Application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and ethylene conversion.

In this description, metric units and parts by weight are employed unless otherwise stated. Various reactor configurations may be used, including fluidized bed catalytic reactors, moving bed and fixed bed reactors.

The MTO process may be optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock. Suitable equipment and operating conditions are described in U.S. patent application Ser. No. 687,045, filed Dec. 28, 1984, incorporated herein by reference.

The process is depicted in FIG. 1, wherein methanol feed is fed to the oxygenate conversion system in the primary stage and the primary stage effluent is separated in a primary fractionation system to recover heavy liquid, byproduct water, ethene-rich light gas and $C_3+$ hydrocarbons, rich in $C_3-C_4$ olefins. The major amount of $C_3-C_4$ olefins is fed to the oligomerization reactor system for upgrading to heavier hydrocarbons, especially $C_{10}+$ distillate range aliphatics and $C_5-C_6$ gasoline which may be produced, fractionated and employed as disclosed in U.S. Pat. No. 4,497,968 (Owen et al), incorporated herein.

The $C_3-C_4$ hydrocarbon stream from the secondary oligomerization fractionation system contains unconverted propene, butylenes and isobutane; however, the relative amounts of these components are not in stoichiometric balance for alkylation. Accordingly, a slipstream of $C_3-C_4$ hydrocarbons, rich in olefins, is taken from the primary fractionation system, and bypasses the oligomerization reactor system. Thus, the alkylation reactor system receives sufficient propene and butylenes to alkylate fresh isoparaffin derived from the oligomerization reactor system.

Figure 2:
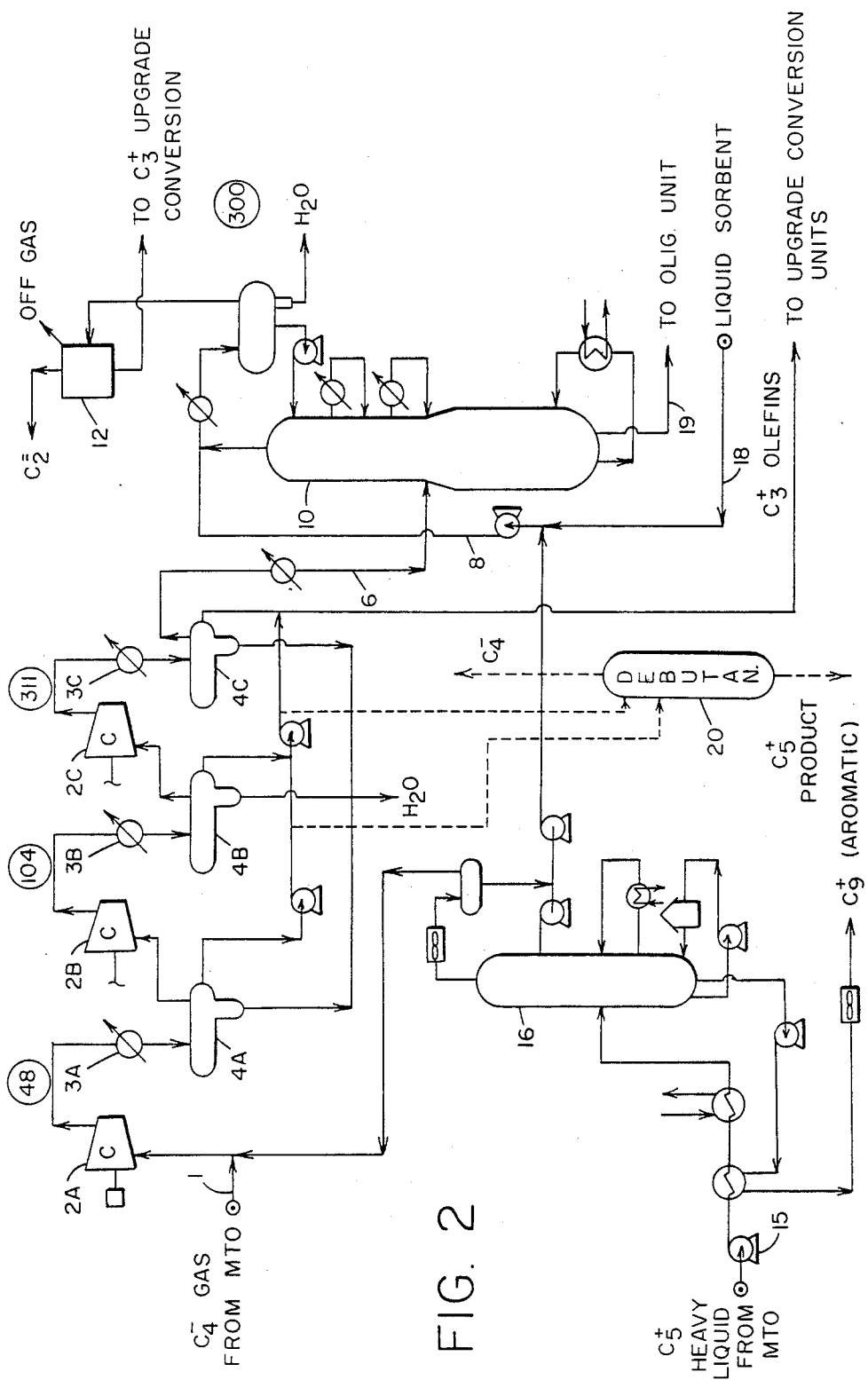
FIG. 2 is a schematic representation of a preferred inter-stage separation system.

In a preferred embodiment depicted in FIG. 2, the primary stage effluent is prefractionated before being sent to olefin upgrading units. Referring to the process diagram of FIG. 2, a gaseous feedstream 1 from an MTO reactor is compressed adiabatically in a series of compressors 3A, B, C and passed through corresponding coolers 3A, B, C and phase separators 4A, B, C to recover byproduct water and condensed hydrocarbons containing various amounts of $C_3-C_5$ aliphatics. An ethene-rich stream 6 is contacted with a liquid sorbent stream 8 in a countercurrent sorption tower 10. Ethene-rich overhead vapor from tower 10 is further purified in cryogenic separation unit 12 to remove lighter gas and $C_3+$ components. The purified ethene may be recovered or recycled to the primary stage MTO reactor for further conversion. The $C_3+$ stream from unit 12 is rich in propene and $C_4$ aliphatics, which may be upgraded by alkylation, by passing the oligomerization reactor.

Heavy liquid separated from the MTO process primary effluent is pressurized by pump 15 and fractionated in tower 16 to recover a $C_9+$ aromatic-rich stream. The condensed overhead, rich in $C_5+$ aliphatic and aromatic components, is combined with other liquid sorbent (e.g., olefinic gasoline) from line 18 and fed via line 8 to absorber unit 10. $C_3+$ components sorbed from the feed are removed from column 10 as olefinic sorbate 19, which is a suitable feed to the oligomerization reactor for upgrading to olefinic distillate and gasoline.

As shown by dashed line, an optional debutanizer tower 20 may be employed to recover $C_5+$ components condensed from the compressor section. The $C_4-$ overhead from tower 20 may be fed to either the oligomerization or alkylation reactor systems for upgrading.

Figure 3:
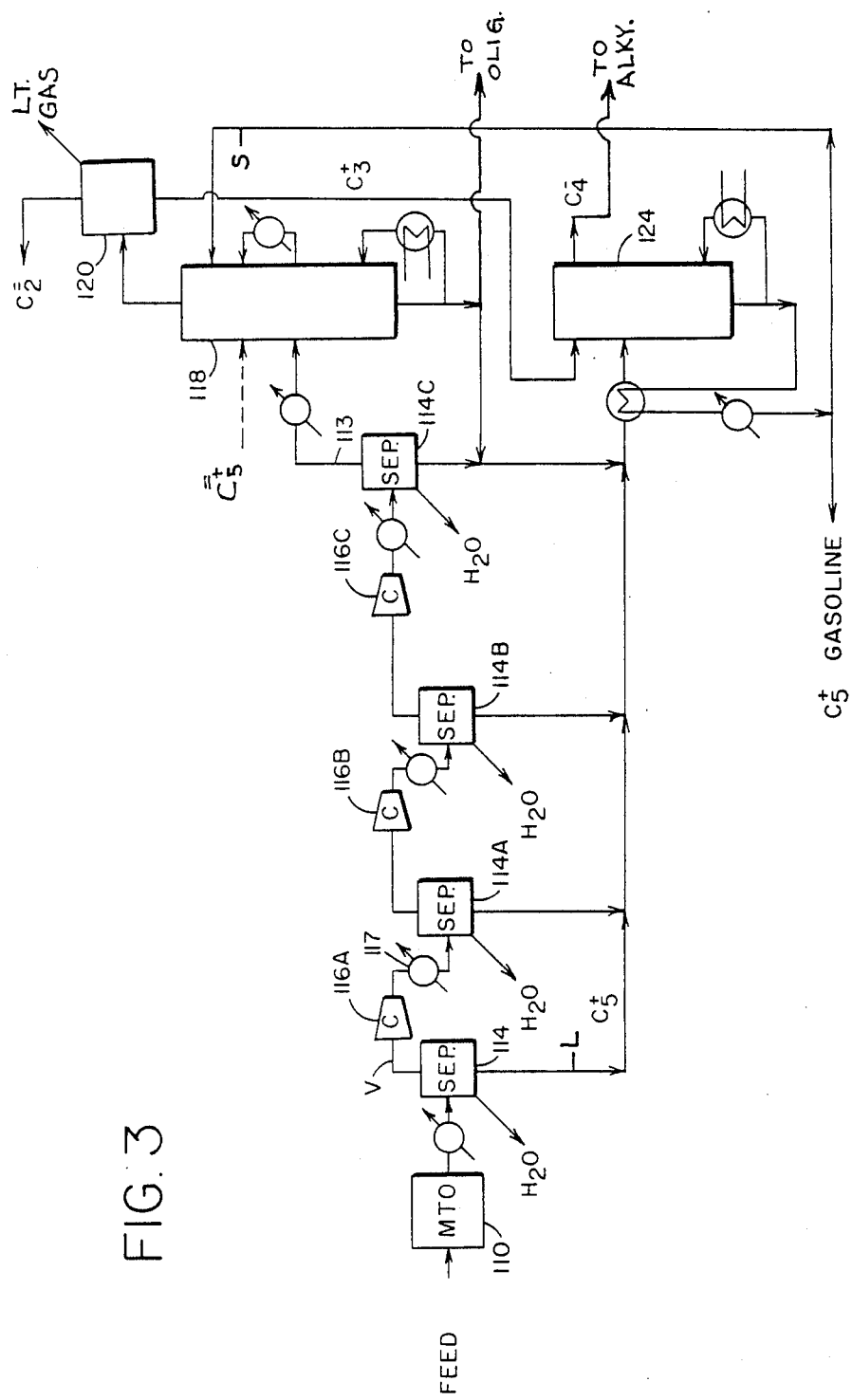
FIG. 3 is an alternative process flow sheet.

In the embodiment of FIG. 3, oxygenate feedstock is converted in MTO unit 110, cooled and passed to separator 114 to provide a $C_5+$ heavy liquid stream L. The light hydrocarbon vapor stream V separated from the primary stage effluent is compressed in a plurality of compression stages to condense liquid olefinic hydrocarbons. The liquid stream L is combined with a $C_3+$-rich condensed liquid from succeeding separators. The primary vapor stream is adiabatically compressed by compressor 116A, cooled by exchanger 117 and passed to a succeeding separator 114A, at which point the preceeding phase separation technique is repeated. Likewise other compressors 116B, C and separators 114B and 114C operate to provide an ethene-rich stream, which is passed via line 119 to sorption fractionation unit 118 and optional cryogenic unit 120. Ethene-rich vapor withdrawn from the separator 114C may be processed to increase ethene purity to at least 40% in sorption unit 118. This can be achieved by selectively absorbing $C_3+$ components in a $C_5+$ liquid hydrocarbon sorbent stream comprising aliphatic and aromatic hydrocarbons generated in the MTO unit. Advantageously, the MTO effluent is received at about atmospheric pressure (e.g., 100–150 kPa) and compressed in plural stages to a pressure of about 1500–3000 kPa and separated in the final vessel 114C at about ambient temperature (20°–80° C.). Olefinic liquids rich in $C_3+$ aliphatics may be recovered from the final compressor stage and passed with $C_5+$ in the liquid hydrocarbon stream L to fractionation tower 124 where $C_5+$ gasoline sorbent 5 and product are recovered. Olefinic gasoline ($C_5-C_9$) may be optionally recycled from the oligomerization stage as additional sorbent if required. A major portion of $C_3-C_4$ olefins may be sent to oligomerization directly from absorber 118. A suitable selective sorption unit is disclosed in U.S. Pat. No. 4,450,311 (Wright et al), incorporated herein by reference.

The alkylation process employed herein is a well known industrial technique for reacting alkenes with tertiary alkanes (isoparaffins), such as isobutane, isopentane, isohexane, etc. The resulting product is a $C_7+$ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21–41 MPa (3000–6000 psi). Under these conditions, both normal and isoparaffins can be brought into reaction by a free-radical mechanism. Thermal alkylation is not known to be practiced commercially.

The catalytic alkylation of paraffins involves the addition of an isoparaffin containing a tertiary hydrogen to an olefin. The process is used in the petroleum industry to prepare highly branched paraffins mainly in the $C_7$ to $C_9$ range, that are high-quality fuels. The overall process is complex, requiring control of operating conditions and of catalyst. The process conditions and the product composition depend on the particular hydrocarbons involved.

The preferred processes are those brought about by the conventional protonic and Lewis catalysts. Propene can be brought into reaction with an isoparaffin in the presence of either concentrated sulfuric acid or hydrogen fluoride. The heptanes produced by alkylation of isobutane with propene are mainly 2,3- and 2,4-dimethylpentane. Propene is alkylated preferably as a component of a $C_3$–$C_4$ fraction. HF catalysts for alkylation of isobutane with 1- and 2-butenes give both dimethylhexanes and trimethylpentanes. The product obtained from alkylation of isobutane with isobutylene at low temperature (e.g., $-25°$ C.) with hydrogen fluoride is 2,2,4-trimethylpentane.

During use the acid catalysts may become diluted with byproduct hydrocarbons and as a result decrease in activity. Sulfuric acid concentrations are maintained at about 90%. Hydrogen fluoride concentrations of 80–90% are common, although the optimum concentration depends on the reaction temperature and reactor geometry. Operation below these acid concentrations generally causes incomplete conversion or polymerization. With sulfuric acid, the product quality is improved when temperatures are reduced to the range of $0°$–$10°$ C. Cooling requirements are obtained by low temperature flashing of unreacted isobutane. With hydrogen fluoride, the reaction process is less sensitive to temperature, and temperatures of $0°$–$40°$ C. can be used. Some form of heat removal is essential because the heat of reaction is approximately $14\times10^5$ J/kg (600 Btu/lb) of butenes converted. Typically the elevated pressure for alkylation by these acid catalysts is about 1500 to 3000 kPa (200–300 psig).

In order to prevent polymerization of the olefin as charged, an excess of isobutane is present in the reaction zone. Isobutane-to-olefin molar ratios of 6:1 to 14:1 are common, more effective suppression of side reactions being produced by the higher ratios.

The typical alkylation reaction employs a two-phase system with a low solubility of the isobutane in the catalyst phase. In order to ensure intimate contact of reactants and catalyst, efficient mixing is provided. This is important with sulfuric acid because of the low solubility of isobutane in the catalyst phase. In addition, the higher viscosity of the sulfuric acid requires a greater mixing energy to assure good contact. The solubility of the hydrocarbon reactants in the catalyst phase is increased by the presence of the unsaturated organic diluent held by the acid catalyst. This organic diluent also has been considered a source of carbonium ions that promote the alkylation reaction.

For the hydrofluoric acid system, reactive i-$C_4H_8$ readily alkylates to give an excellent product. The alkylation of pure 1-$C_4H_8$ by itself proceeds with considerable isomerization of the 1-$C_4H_8$ to 2-$C_4H_8$ followed by alkylation to give a highly branched product. The presence of i-$C_4H_8$ accelerates the alkylation reaction and allows less time for olefin isomerization. Consequently the reaction produces an alkylate with a lowered antiknock value. For the sulfuric acid system, i-$C_4H_8$ tends to oligomerize and causes other side reaction products of inferior quality; but the isomerization of 1-$C_4H_8$ to 2-$C_4H_8$ proceeds more completely, thereby favoring formation of superior products. Thus for mixed olefin feeds such as described above, the two factors with both catalyst systems counteract each other to provide products of similar antiknock properties.

The olefin-producing MTO process may simultaneously generate isobutane, but the amount may be insufficient to alkylate the coproduced olefins. A suitable outside source of isobutane is natural gas or a byproduct of methanol-to-gasoline (MTG) processes.

Suitable alkylation processes are described in U.S. Pat. Nos. 3,879,489 (Yurchak et al), 4,115,471 (Kesler), 4,377,721 (Chester) and in the Kirk-Othmer Encyclopedia of Chemical Technology, Vol. 2, pp. 50–58 (3rd Ed., 1978) John Wiley & Sons, incorporated herein by reference.

The combined processes are an effective means for converting oxygenated organic compounds, such as methanol, DME, lower aliphatic ketones, aldehydes, esters, etc, to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific example, there is no intent to limit the inventive concept as set forth in the following claims.

We claim:

1. A continuous catalytic process for converting olefinic feedstock comprising ethylene and $C_3+$ olefins to heavier liquid hydrocarbon product comprising the steps of
   prefractionating the olefinic feedstock to obtain a gaseous stream rich in ethylene and an olefinic stream containing $C_3+$ olefin;
   contacting a major portion of the $C_3+$ stream from the prefractionating step with shape selective medium pore zeolite oligomerization catalyst in a distillate mode catalytic reactor zone at elevated temperature and pressure to provide a heavier hydrocarbon effluent stream comprising distillate, gasoline and lighter hydrocarbons;
   fractionating the effluent stream to recover distillate, gasoline and $C_3$–$C_4$ hydrocarbon stream containing isobutane;
   further reacting isobutane from the $C_3$–$C_4$ hydrocarbon stream with a second portion of $C_3+$ olefin from the prefractionating step in an alkylation reactor zone in the presence of acid alkylation catalyst to produce $C_7+$ alkylate.

2. The process of claim 1 wherein the alkylation catalyst comprises hydrofluoric acid and the alkylation reactor is operated at pressure of about 1500 to 3000 kPa to provide a liquid reaction phase.

3. The process of claim 1 wherein the olefinic feedstock is produced in a primary stage by converting an oxygenated lower aliphatic compound to hydrocarbons by contacting the oxygenated compound with at least one catalyst comprising acidic zeolite at elevated temperature and moderate pressure to convert at least a portion of the oxygenate to hydrocarbons containing a major fraction of $C_2$–$C_5$ olefins and a minor fraction containing $C_5+$ heavy hydrocarbon.

4. A continuous process for upgrading $C_3$–$C_4$ hydrocarbon feed containing olefins to produce heavier liquid hydrocarbons comprising converting a major portion of $C_3$–$C_4$ olefins in an oligomerization zone by contacting a shape selective medium pore zeolite catalyst at elevated temperature and pressure to make distillate and olefinic gasoline;

fractionating the oligomerization stage effluent to provide distillate and gasoline product and a $C_3$–$C_4$ intermediate stream containing isobutane and unconverted propene and butylene; and combining the $C_3$–$C_4$ intermediate stream with a portion of $C_3$–$C_4$ feed and further converting the combined streams in an alkylation zone to make heavier paraffinic hydrocarbons.

* * * * *